(12) United States Patent
Decho et al.

(10) Patent No.: US 8,546,071 B2
(45) Date of Patent: Oct. 1, 2013

(54) HIGH-THROUGHPUT IN VITRO TRANSLATION (CELL-LYSATE BASED) ASSAY FOR DETECTING QUORUM SENSING SIGNALS

(75) Inventors: Alan W. Decho, Columbia, SC (US); Tomohiro Kawaguchi, Columbia, SC (US); Yung-pin Chen, Columbia, SC (US)

(73) Assignee: University of South Carolina, Columbia, SC (US)

( * ) Notice: Subject to any disclaimer, the term of this patent is extended or adjusted under 35 U.S.C. 154(b) by 1128 days.

(21) Appl. No.: 12/180,857

(22) Filed: Jul. 28, 2008

(65) Prior Publication Data

US 2012/0164672 A1   Jun. 28, 2012

Related U.S. Application Data

(60) Provisional application No. 60/962,323, filed on Jul. 27, 2007, provisional application No. 60/964,098, filed on Aug. 9, 2007.

(51) Int. Cl.
  *C12Q 1/00* (2006.01)
(52) U.S. Cl.
  USPC .............. 435/4; 435/7.2; 435/7.32; 435/7.75; 435/34

(58) Field of Classification Search
  None
  See application file for complete search history.

(56) References Cited

PUBLICATIONS

Gonzalez et al (Microbiol. Research. 2001. 15594): 271-277).*
Fuqua et al (J.Bacteriol. 1996. 178: 435-440).*
Kumari et al (Anal Chem. 2006. 78: 7603-9).*
Shaw et al (PNAS. Jun. 1997. 94(12): 6036-41).*
Promega: http://www.ebiotrade.com/buyf/productsf/Promega/tm239.pdf 2003.*

* cited by examiner

*Primary Examiner* — Jennifer Graser
(74) *Attorney, Agent, or Firm* — Dority & Manning, P.A.

(57) ABSTRACT

A cell-lysate extract based assay reagent for detecting quorum sensing signals is generally provided, along with methods of making and using the same. The assay reagent generally includes a cell-lysate extract formed from a biosensor bacterium (e.g., *Agrobacterium tumefaciens* NTL4 (pCF218) (pCF372)) and a detecting substrate (e.g., an absorbance-based or luminescence-based substrate). The cell-lysate extract can be prepared by (1) disrupting the cell membranes of the biosensor bacterium to release the cellular components into a solution, (2) centrifuging the resulting solution, and (3) removing the resulting supernatant solution.

17 Claims, 6 Drawing Sheets

HIGH-THROUGHPUT IN VITRO TRANSLATION (CELL-LYSATE BASED) ASSAY FOR DETECTING QUORUM SENSING SIGNALS

PRIORITY INFORMATION

The present disclosure claims priority to U.S. Provisional Patent Application Ser. No. 60/962,323 filed on Jul. 27, 2007 and U.S. Provisional Patent Application Ser. No. 60/964,098 filed on Aug. 9, 2007, the disclosures of which are incorporated by reference herein.

GOVERNMENT SUPPORT CLAUSE

The present invention was developed with funding from National Science Foundation's Collaborative Research in Chemistry (CHE-0526821) and NSF Environmental Genomics Program (EF-0723707). The government retains certain rights in this invention.

BACKGROUND OF INVENTION

Quorum sensing (QS) is an emerging research field in health and environmental sciences during past decade. QS is the ability of bacteria to communicate and coordinate behavior such as biofilm formation via signaling molecules called autoinducers (e.g. acyl-homoserine lactones (AHLs)), and is now known to be involved in many microbial disease and biofouling processes. Therefore, it is conceivable that quorum sensing inhibition represents a new, novel strategy to disrupt biofilm formation to combat microbial diseases.

A simple, sensitive and rapid assay for the detection of AHLs is urgently needed in quorum sensing research. There are many methods developed to detect AHLs, such as whole cell assays using biosensors, thin-layer chromatography (TLC), gas chromatography (GC), high performance liquid chromatography (HPLC), and liquid chromatography/mass spectrometry (LC/MS). Among those methods, whole-cell bioassays, such as the reporter bacterium *Agrobacterium tumefaciens* NTL4 (pCF218)(pCF372), have been a most popular and sensitive method because these methods don't require expensive instruments (such as in HPLC and LC/MS). However, there are disadvantages of the whole-cell bioassay: 1) it requires relatively labor intensive cell conditioning, 2) it takes at least 24 hours for detection of AHLs, 3) it may be difficult to screen the inhibitors of QS when the test substance inhibits cell growth itself and 4) it is qualitative and does not provide accurate and precise quantification.

The in-vitro synthesis of proteins in cell-lysate extracts has been an important tool for molecular biologists and has a variety of applications including rapid identification of gene products (e.g. proteomics), localization of mutations through synthesis of truncated gene products, protein folding studies, and incorporation of modified or unnatural amino acids for functional studies. The most frequently-used cell-free translation systems consist of extracts from rabbit reticulocycles, wheat germ and *Escherichia coli*. All are prepared as crude extracts containing all the macromolecular components (e.g. 70S or 80S ribosomes, tRNAs, aminoacyl-tRNA synthetases, initiation, elongation and termination factors, etc.) required for translation of exogenous RNA.

As such, a need exists for an improved method of sensing AHLs. The present disclosure seeks to address the disadvantages of prior art construction and methods, and presents a high-throughput in-vitro translation (cell-lysate based) assay system for detection of QS chemical signals.

SUMMARY OF INVENTION

Objects and advantages of the invention will be set forth in part in the following description, or may be obvious from the description, or may be learned through practice of the invention.

In one embodiment, the present invention relates to the use of a high-throughput in-vitro translation for detection of QS chemical signals (e.g., AHLs) using the cell-lysate extract derived from an AHL-reporter bacterium. With this system, many samples can be screened for the presence of AHLs using microtiter plates by simple addition of cell-lysate extract derived from a biosensor bacterium. AHLs can be detected using a microplate reader (or fluorometer) within a short period of time (some measurements within 3 hours). This assay system eliminates a time-consuming cell conditioning before each assay. Also, the cell-lysate extract can be stored in a $-20°$ C. freezer for long periods of time.

Additional advantages of the invention will be set forth in part in the description which follows or may be learned by practice of the invention. It is to be understood that both the foregoing general description and the following detailed description are exemplary and explanatory only and are not restrictive of the invention.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

DETAILED DESCRIPTION OF INVENTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Generally speaking, the present invention is directed to an in-vitro translation (cell-lysate extract) based assay system for detecting quorum sensing signals that eliminates a time-consuming biosensor cell conditioning step required before a whole cell bioassay. The assay system includes the following steps: (1) Preparation of a cell-lysate extract (CLE) from a biosensor bacterium (e.g. Agrobacterium tumefaciens NTL4 (pCF218)(pCF372)); (2) incubation of samples with CLE; (3) addition of an absorbance-based substrate (e.g. 5-bromo-4-chloro-indolyl R-D-galactopyranoside (X-Gal)) or luminescent substrate (e.g. β-Glo) to samples; (4) incubation; and (5) measurement of absorbance or luminescence.

This system and assay procedure is substantially quicker and easier to perform than other known methods and systems, particularly since the preparation of the CLE can be performed at an earlier time and stored for later use. Thus, detection can be performed quickly upon receipt of a sample. Also, the response created by the system and method can be detected in a short time (e.g., about 3 hours) after incubation of the sample with the CLE.

The system and methods can be suitable to screen not only a quorum sensing colony and quorum sensing inhibitors but also acyl-homoserine lactones (AHLs) receptor proteins and co-factors in a large number of samples using a 96 well plate in quorum sensing research. Also, this method is simple and cost-effective and can be easily applied for the presence of AHLs in environmental samples in the field condition. Since this method uses the cell-lysate extract system, it provides a great educational tool for students to understand the process of quorum sensing.

The present invention has many different uses, including but not limited to, rapid and high-throughput screening of communication signals (e.g. AHLs), detection of analogs and inhibitors of communication signals, biochemical studies of LuxR or TraR proteins, determining effects of various chemical substances on AHL activity, or it can be used in protein expression and isolation studies. The invention can also be used as an educational kit for teaching cell-to-cell communication.

A. Preparation of a Cell-Lysate Extract CLE from a Biosensor Bacterium

In accordance with the present invention, a cell-lysate extract (CLE) is produced using a biosensor bacterium. The resulting cell-lysate extract can be utilized in an in vitro translation assay for detecting quorum sensing signals.

The CLE, in one particular embodiment, can be produced according to a centrifuge technique. An exemplary centrifuge technique typically involves centrifuging the cell culture to create cell pellets that can then be collected. Centrifuging the cell culture can be performed at any speed sufficient to form cell pellets, such as from about 2,000 rpm to about 25,000 rpm for at least about 5 minutes. For instance, the cell culture can be centrifuged at a speed of about 5,000 rpm to about 15,000 rpm for about 5 minute to about 60 minutes, such as about 10,000 rpm for about 10 min.

Once the cell pellets are created and collected, the cell membranes can be disrupted via cell disruption methods to release the contents of the cell into the solution. For example, sonication methods can be used to disrupt the cell and release the cell contents. Sonication generally involves applying sound (e.g., ultrasound) energy to agitate particles in a sample, in this case, the cell walls of the biosensor bacterium. It can be applied using an ultrasonic bath or an ultrasonic probe, colloquially known as a sonicator. According to this method, sonication is sufficient to disrupt or deactivate a biological material by disrupting the cell membranes and releasing the cellular contents. Sonication was performed by Microson™ XL 2000 (Misonix inc.) for 30 sec. three times at 20 kHz at room temperature.

Of course, cell disruption methods other than sonication can be utilized, including but not limited to enzymatic methods, bead methods, detergent methods, solvent use, rapid decompression (a.k.a., the "French pressure cell"), high-shear mechanical methods, and the like. Enzymatic methods utilize enzymes (e.g., lysozyme, lysostaphin, zymolase, cellulase, mutanolysin, glycanases, proteases, mannose, etc.) to disrupt the cell wall and release the cell contents. Bead methods utilize small beads (e.g., glass beads, ceramic beads, steel beads, etc.) in combination with a high level of agitation (e.g., stirring, shaking, etc.) to disrupt the cell walls and release the contents of the cell. Detergent methods can be utilized to disrupt the cell wall by disrupting lipid:lipid, lipid:protein and protein:protein interactions with the detergent. The detergent can be nonionic or zwitterionic, although ionic detergents are preferred. A rapid decompression or "French pressure cell" method disrupts the cell wall by placing the cells under high pressure (usually nitrogen or other inert gas up to about 25,000 psi) and then rapidly releasing the pressure. The rapid pressure drop causes the dissolved gas to be released as bubbles that ultimately lyse the cell. High-shear mechanical methods for cell disruption fall into three major classes: rotor-stator processors, valve-type processors, fixed-geometry fluid processors. These processors all work by placing the bulk aqueous media under shear forces that literally pull the cells apart.

No matter the cell disruption technique utilized, the cell pellets can be disrupted to release the cellular contents in a buffered aqueous solution, where the pH is balanced from about 5 to about 9, such as from about 6 to about 8. The buffered aqueous solution can preferably have a pH of about 7 in most applications. The buffered aqueous solution can include a buffering agent to control the pH of the solution. One particularly suitable buffering agent that can be included within the buffered aqueous solution is $KH_2PO4$, although any suitable buffering agent can be employed.

Once the cell membranes have been disrupted and the cell contents released into an aqueous solution, the aqueous solution can be centrifuged (e.g., at about 50,000 rpm for 30 minutes) to separate the released cell contents from the cell wall and membranes. Upon centrifuging this aqueous solution, the supernatant solution will contain the cell contents that can be separated from the cell wall membranes. Thus, the supernatant solution becomes the CLE solution (e.g., the assay reagent) configured to detect the presence of AHLs.

One advantage of the CLE solution produced according to the present invention is that the solution can be frozen and stored with relative ease. For example, the CLE solution can be stored at a temperature of less than about 0° C. since the solvent of the solution is water. For instance, storage temperatures can be from about −5° C. to about −50° C., such as from about −10° C. to about −30° C.

Additionally, the CLE solution can be utilized to detect quorum sensing signals without the addition of any other materials or compositions. Thus, the CLE solution formed from the biosensor bacterium can contain all the necessary components for in vitro detection. These components can include, but are not limited to, 70S ribosome; tRNAs; aminoacyl-tRNA sunthetases; initiation, elongation, and termination factors; amino acids; ATP; GTP; and cofactors (e.g., $Mg^{2+}$ and $K^+$.

The biosensor bacterium used to form the CLE can be selected from those biosensor bacterium configured to detect the presence of AHL. One particularly suitable biosensor bacterium for use in the present invention is *Agrobacterium tumefaciens* NTL4 (pCF218)(pCF372). *Agrobacterium tumefaciens* NTL4 (pCF218)(pCF372) is disclosed in greater detail by Fuqua and Winnas, 1996, J. Bac. 178: 435-440. *Agrobacterium tumefaciens* NTL4 (pCF218)(pCF372) may be obtained from the Dept. of Biology of the Indiana University, Bloomington. *Agrobacterium tumefaciens* NTL4 (pCF218)(pCF372) contains the β-galactosidase gene driven by a traI promoter, allowing the expression of β-galactosidase to be regulated by the presence of quorum sensing signals (e.g., AHLs).

Other biosensor bacterium that may be utilized to form the CLE according to the present disclosure are discussed in Steindler, et al., "Detection of quorum-sensing N-acyl homoserine lactone signal molecules by bacterial biosensors", FEMS Microbiol Lett. 266 (2007) pg. 1-9, which is incorporated by reference to the extent that it does not contradict the present disclosure (see e.g., Table 1).

It should be noted that not all biosensor bacterium may be utilized to form a CLE suitable for detecting and indicating the presences of AHLs. For example, the present inventors have discovered that CLE formed from *A. tumefaciens* KYC55, *Vibrio harveyi* BB120, and *Vibrio harveyi* BB886 did not satisfactorily indicate the presence of AHLs.

The biosensor bacterium can be grown into a culture according to any method in order to provide a sufficient amount of biosensor bacterium for producing the CLE solution according to the present invention.

B. Detection of Quorum Sensing Signals

Once formed, the CLE solution formed can be utilized to detect the presence or absence of quorum sensing signals. Two particular methods of detecting the presence of AHLs are particularly suitable for use with the present invention: absorbance assays and luminescence assays. In either of these methods, a detecting substrate (absorbance-based substrate or luminescence-based substrate) is added to the CLE solution to form the assay reagent.

In an absorbance assay, an absorbance-based substrate can be added to the CLE solution to give a spectral response upon contact with AHLs. For example, 5-bromo-4-chloro-3-indolyl-β-D-galactopyranososide (X-Gal can be added to the CLE solution. When the biosensor bacterium *Agrobacterium tumefaciens* NTL4 (pCF218)(pCF372) is utilized to form the CLE solution, the β-galactosidase enzymatically cleaves to 5-bromo-4-chloro-3-indolyl-β-D-galactopyransoside (X-Gal), which results in its conversion to a blue precipitate when active forms or AHLs are present. Accumulation of the blue precipitate is then detectable by spectral absorbance at 635 nm. In one embodiment, a spectrophotometer can be used to measure the absorbance.

Alternatively, a luminescence-based substrate (e.g., 6-O-β-galactopyranosyl luciferin) can be added to the CLE solution to give a luminescence response upon contact with AHLs. One particularly suitable luminescence-based detector is available commercially under the name Beta-Glo (Promega Corporation, Madison Wis.), which uses a coupled enzyme reaction in which the luminescence-based substrate (6-O-β-galactopyranosyl luciferin) is cleaved by β-galactosidase to yield free luciferin that is used in a reaction catalyzed by luciferase to generate a luminescent signal proportional to the amount of β-galactosidase present. The present inventors have also discovered that the use of a luminescence-based substrate may increase the sensitivity of the CLE solution to AHLs when compared to absorbance based assays using X-Gal.

Any other suitable method can be utilized to report the detection of the quorum sensing signals by the CLE solution formed according to the present invention.

EXAMPLES

The following experiment is provided to illustrate the present invention (i.e. cell-lysate extract assay for AHLs detection) and is not intended to limit the scope of the invention. This illustration constitutes a "detection-assay" based on cell-free lysate of a biosensor bacterium, *Agrobacterium tumefaciens* NTL4 (pCF218)(pCF372), for detection of quorum sensing signals called acylated homoserine lactones (AHLs). More details of this example can be found in Kawaguchi, et al. "Rapid Screening of Quorum-Sensing Signal N-Acyl Homoserine Lactones by an In Vitro Cell-Free Assay" Appl. Environ. Microbial. Vol. 74, No. 12 p. 3667-3671 (June 2008), the disclosure of which is incorporated by reference herein.

The general protocol followed was
Absorbance Assay
1) A culture of *A. tumefaciens* NTL4 (pCF218)(pCF372) was grown in 250 ml of AT minimal glucose media plus streptomycin (50 μg/ml) and tetracycline (5 μg/ml) at 30° C. with shaking for 18 hrs.
2) The resulting cell culture was centrifuged at 10,000 rpm for 10 min. to collect cell pellets.
3) The collected cell pellets were sonicated in 8 ml of 0.1 M $KH_2PO4$ (pH 7.0) buffer to produce a homogenate.
4) The sonicated homogenate was centrifuged at 50,000 rpm for 30 min. and the supernatant solution was collected.
5) The supernatant solution was stored at −20° C. until the experiment.
6) 50 μl of a sample solution containing AHLs was added to the wells of a 96-well plate.
7) 50 μl of the collected supernatant solution from step (5), along with 100 μl of 20 mM $KH_2PO_4$, was added and mixed to each sample, and each sample was incubated at 30° for 2 h.
8) 1 μl of X-Gal (20 mg/ml) was added and mixed into each well, and each sample was incubated at 30° C. for 1 h.
9) The absorbance of each well was read at 635 nm.

Luminescence Assay
From step 5)
6) 50 μl of sample solution containing AHLs was added in 96-well plate.
7) 50 μl of assay reagent diluted in 20 mM $KH_2PO4$ was added into each well, mix and incubate at 30° for 2 h.
8) 100 μl of an appropriate luminescent substrate (e.g. β-Glo, Promega) was added into each well, mix and incubate and incubate at 30° C. for 1 h.
9) luminescence was read by microplate luminometer (e.g. Veritas Turner BioSystems).

This experiment is discussed in greater detail below.

Materials and Methods

Bacterial Strain and Growth Conditions.

The reporter strain *A. tumefaciens* NTL4 (pCF218) (pCF372) lacks the Ti plasmid, and contains two plasmids, (pCF218) and (pCF372), that encode the traR and a traI-lacZ fusion genes, respectively. This system provides extremely-sensitive detection of AHLs. Professor W. Clay Fuqua, Indiana University, generously provided the strain for our assay. Cultures of *A. tumefaciens* NTL4 (pCF218)(pCF372) were grown in 250 ml vessels using AT minimal glucose media (35) containing 0.5% (w/v) glucose, 0.079 M $KH_2PO_4$, 0.015 M $(NH_4)_2SO_4$, 0.6 mM $MgSO_4.7H_2O$, 0.06 mM $CaCl_2.2H_2O$, 0.027 mM $FeSO_4.7H_2O$, 0.0071 mM $MnSO_4.H_2O$ in distilled $H_2O$ and adjusted with 1 N NaOH to pH 7.0. The antibiotics streptomycin (50 μg/ml) and tetracycline (5 μg/ml) were also added.

N-Acylhomoserine Lactones.

The N-acylhomoserine lactones: N-butanoyl-homoserine lactone ($C_4$-AHL), N-hexanoyl-homoserine lactone ($C_6$-AHL), N-heptanoyl-homoserine lactone ($C_7$-AHL), N-octanoyl-homoserine lactone ($C_8$-AHL), N-decanoyl-homoserine lactone ($C_{10}$-AHL), N-dodecanoyl-homoserine lactone ($C_{12}$-AHL), N-tetradecanoyl-homoserine lactones ($C_{14}$-AHL), N-3-oxo-hexanoyl-homoserine lactone (3-oxo-$C_6$-AHL) and N-3-oxo-octanoyl-homoserine lactone (3-oxo-$C_8$-AHL) were purchased from Sigma-Aldrich (St. Louis, Mo., USA) and used for development of the cell-free assay system. $C_8$-AHL was used for final optimization of the cell-free assay system.

Preparation of Cell-Free Lysate.

One liter of the reporter strain was grown in AT minimum glucose media (30° C. with shaking for 18 h) to early exponential-phase and then harvested by centrifugation (12,000× g; 10 min). Cell pellets were collected and resuspended in 5 ml of $KH_2PO_4$ buffer (100 mM; pH 7.4), then sonicated for 30 sec. three times and centrifuged (12,000×g) at 4° C. for 30 min to remove particulate cell fragments. The supernatant was collected as the 'cell-free lysate (CFL)' reagent, and was stored (−80° C.) until use.

Confirmation of β-Galactosidase Expression In Vitro Cell-Free Solution.

To confirm β-galactosidase expression in cell-free solution, the following simple absorbance assay for AHLs was used. The protocol involved: 1) addition of 50 μl of sample solution containing AHLs into a 96-well plate; 2) addition of 50 μl of cell-free extract and 100 μl of 20 mM $KH_2PO_4$ (pH 7.0) into each well, followed by mixing and incubation at 30° C. for 2 h; 3) addition of 1 μl of X-Gal (20 mg/ml) into each well, then mixing and incubation at 30° C. for 1 h; and 4) measurement of absorbance in each well at 635 nm by spectrophotometer (Shimadzu UV-2401 PC UV-VIS, Shimadzu Corp.). To determine the detection limits, 1:1 serial dilutions of each AHL in 20 mM $KH_2PO_4$ (pH 7.0) buffer were performed in triplicate. Induction of β-galactosidase activity was calculated by dividing the absorbance of samples by those of controls. An induction ratio greater than 3 was considered active.

Components Required for Reactions 1) Through 3).

In order for the assay to detect AHLs in a concentration-dependent manner, a series of reactions that are normally restricted to the confines of the cell must also be able to occur in the cell-free assay. These reactions include: 1) binding of AHLs with the receptor protein TraR; 2) binding of TraR/AHL complex to the traR promoter driving the expression of the β-galactosidase gene; and 3) translation of mRNA for the synthesis of β-galactosidase. The following experiments were conducted to confirm that the above reactions were occurring in the cell-free assay.

In order to determine if constitutive production (reactions 1 through 3) of β-galactosidase was occurring within the cell-free extract (i.e. in the absence of added AHLs), assays were carried out with/without added N-octanoyl-homoserine lactone (hereafter $C_8$-AHL), X-Gal, and $C_8$-AHL+X-Gal combinations. The treatments (in triplicate) consisted of added: [$C_8$-AHL]; [X-Gal]; [$C_8$-AHL+X-Gal]; [cell-lysate+$C_8$-AHL]; [cell-lysate+X-Gal]; and [cell-lysate+$C_8$-AHL+X-Gal]. Concentrations of $C_8$-AHL in 20 mM $KH_2PO_4$ (pH 7.0) were 1 μM. Absorbance was measured at 635 nm, and compared for each treatment.

Inhibition of Reaction 1).

In order to show that blocking traR binding of AHL inhibits β-galactosidase expression, high temperature (i.e. 60° C.) was used to degrade most proteins including the TraR protein, which was required for transcription of β-galactosidase gene. Cell-free lysates were heated for 30 min. at 30° C., 40° C., 50° C., 55° C. and 60° C., respectively, prior to the assay. Once the cell-free lysates had cooled to 30° C., $C_8$-AHL standards were added at a concentration of 1 μM with replicates, and incubated. Then, expression of β-galactosidase was measured using the absorbance assay protocol.

Inhibition of Reactions 2) and 3).

To artificially inhibit binding of the AHL/traR complex to the β-galactosidase promoter, we utilized the aminoglycoside antibiotic streptomycin, which precipitates DNA therefore inhibiting the binding of AHL/TraR complex to β-galactosidase promoter. First, 50 μl aliquots of 1 μM $C_8$-AHL solution was added to each tube, followed by addition of cell-free extract. Further, a series of increasing concentrations of streptomycin (i.e. 0, 50, 125, 250, 300 μg) were added to the cell-free extract and incubated for 30 min. prior to the assay (4, 22, 29). Then, β-galactosidase expression was measured by absorbance.

Optimization of Cell-Free Assay.

In order to optimize cell-free assay conditions, the following experiments were conducted. All optimization experiments used the $C_8$-AHL (1 μM).

Crude Protein Concentration in a Cell-Free Assay Solution.

Initially, protein concentrations of undiluted cell-free extract were determined by the Bradford protein assay. Then, cell-free extract (30 μg/ml) was diluted with 20 mM $KH_2PO_4$ (pH 7.0) buffer to 12 μg/ml and 6 μg/ml, respectively. Absorbance-based measurements were conducted using the cell-free assay system to determine the effect of protein concentration in cell-free extracts on β-galactosidase expression.

Optimum pH.

In order to assess the effect of pH on the cell-free assay, triplicate assay solutions were adjusted to pH 4.5, 5.0, 5.4, 6.5, 7.0, 8.0, and 8.8, respectively. Then, cell-free assay absorbances were measured.

Incubation Time.

To determine the effect of incubation time of assay measurements, triplicate cell-free extract solutions were spiked with $C_8$-AHL (1 µM), then incubated for different time periods (1, 2, 3, and 4 h). Then, X-Gal was added to each solution, incubated at 37° C. for 1 h and absorbance (635 nm) was measured.

Comparison of Absorbance and Luminescence Assays.

To improve the sensitivity of the cell-free approach, a luminescence assay was developed for AHLs. The protocol involved: 1) addition of 50 µl of sample solution containing AHLs into a 96-well plate; 2) addition of 50 µl of cell-free extract, diluted in 20 mM $KH_2PO_4$ buffer (pH 7.0) resulting in a protein concentration of 80 µg/ml for each well, and then mixed and incubated at 30° for 2 h; 3) addition of 100 µl of β-Glo® (Promega) into each well, followed by mixing and incubation (30° C. for 1 h); and 4) measurement of luminescence using a Veritus Microplate Luminometer (Turner BioSystems). For control wells, 20 mM $KH_2PO_4$ (pH 7.0) buffer was used. To determine the detection limit, a 1:1 serial dilution of each AHL was performed in triplicate using 20 mM $KH_2PO_4$ (pH 7.0) buffer. Then, absorbance assays were conducted. Induction of β-galactosidase activity was calculated by dividing the sample absorbance or luminescence with that of controls. An induction ratio greater than 3 was considered active (27).

Application of Cell-Free Assay for High-Throughput Screening Clones of Genomics Clones for the Identification of Putative N-Acyl-Homoserine Lactone Genes.

To test the applicability of the cell-free assay for detecting N-acyl-homoserine lactone genes, we used the assay to screen a genomic library derived from a sulfate reducing bacterium (SRB) isolated from marine stromatolites at Highborne Cay, Bahamas. The SRB strain was identified as *Desulfovibrio* sp. H2.3jLac (GenBank Accession #DQ822786). To identify the genes involved in *Desulfovibrio* sp. H2.3jLac quorum sensing, genomic DNA was extracted and a fosmid-based genomic library was constructed. The fosmid library was subsequently screened using the cell-free assay, described above, to identify regions within the *Desulfovibrio* genome that may play a role in QS. Five hundred fosmid clones were grown overnight in 96 well plates followed by the addition of 20 µl of cell-free extract. Plates were incubated for 2 h followed by the addition of 1 µl (20 mg/ml) of X-Gal, then further incubated overnight at 37° C. and clones producing a blue color were scored as positive for putative QS gene activity. Production of AHLs by positive clones was confirmed by LC/MS mass spectrometry. Briefly, positive clones were grown in Marine Broth at 37° C. Culture supernatants were extracted with acidified ethyl acetate, dried and reconstituted with 50% acetonitrile. AHLs in samples were separated by HPLC using a 2.1 mm×150 mm Aquasep C18 column (ES Industries). The separation was performed using a binary gradient of two solvents (Solvent A: $H_2O$ with 0.1% (w/v) formic acid; Solvent B: acetonitrile with 0.1 formic acid). Initially, gradient conditions were 20% Solvent A for 2 minutes, then was linearly ramped (28 minutes) to 100% Solvent B. AHLs were detected using Waters Premier XE triple quadrupole mass spectrometry with positive ion electrospray ionization. The triple quad mass spectrometer was operated in multiple reaction monitoring mode utilizing two characteristic fragment transitions per analyte.

Results

Confirmation of β-Galactosidase Expression Upon Addition of AHLs In Vitro Cell-Free Solution.

Figure 1:
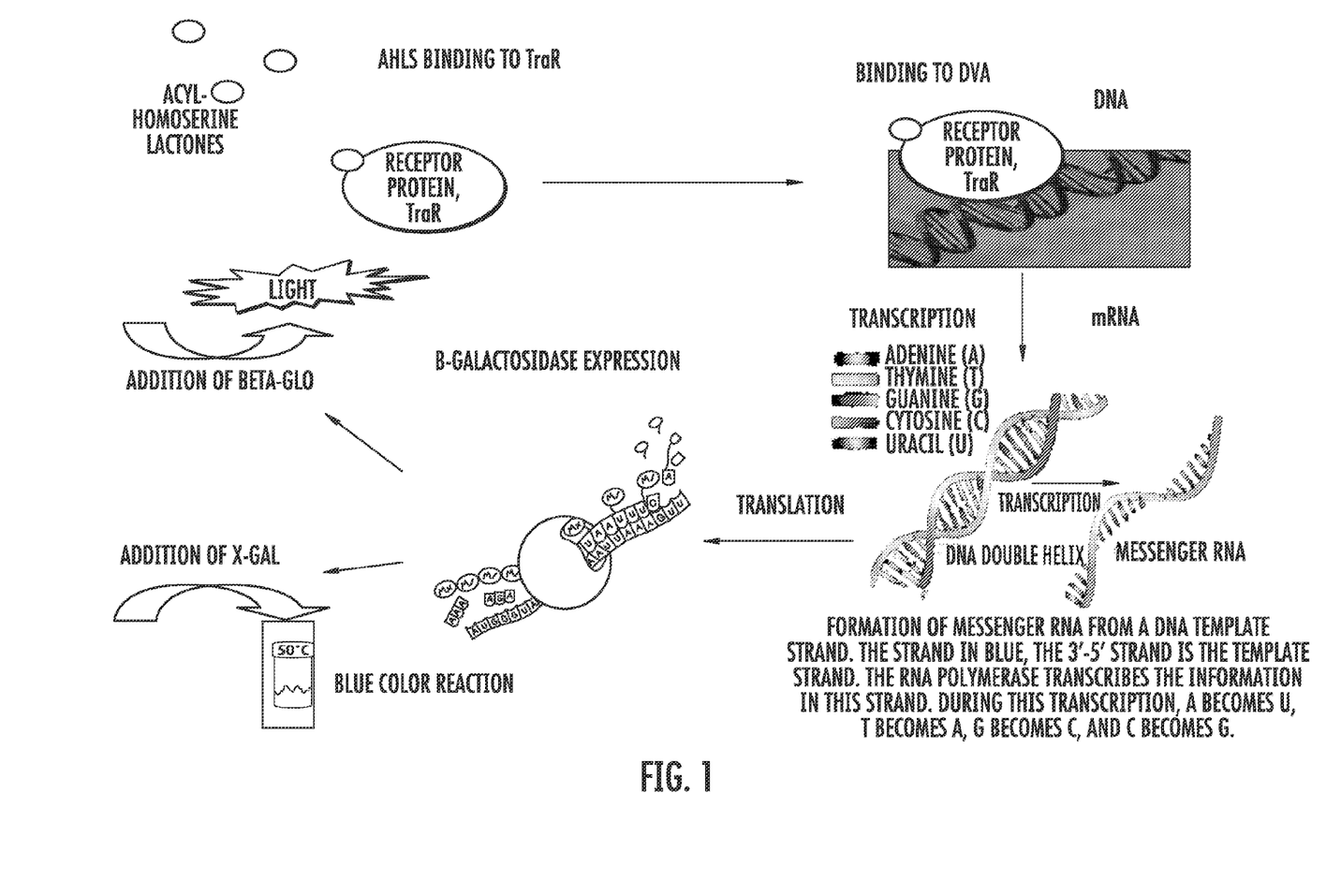
FIG. 1 depicts a cell-lysate extract based system for detection of AHLs.
Figure 2:
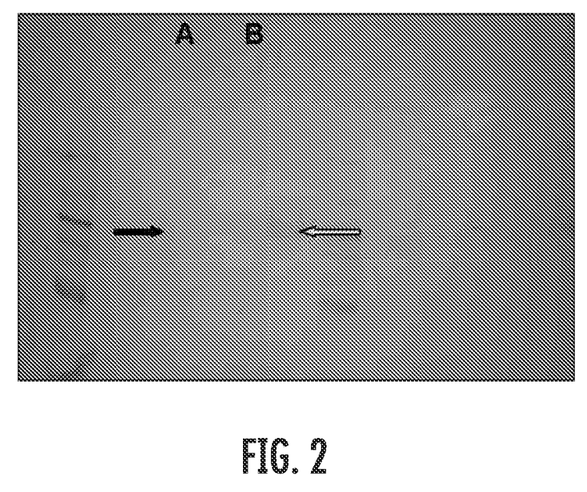
FIG. 2 shows a western blot of β-galactosidase being expressed in cell-free assay system (Lane A) by the addition of acyl-homoserine lactone (AHL-C8) after 2 hours of incubation. Lane B is the β-galactosidase standard.
Figure 3:
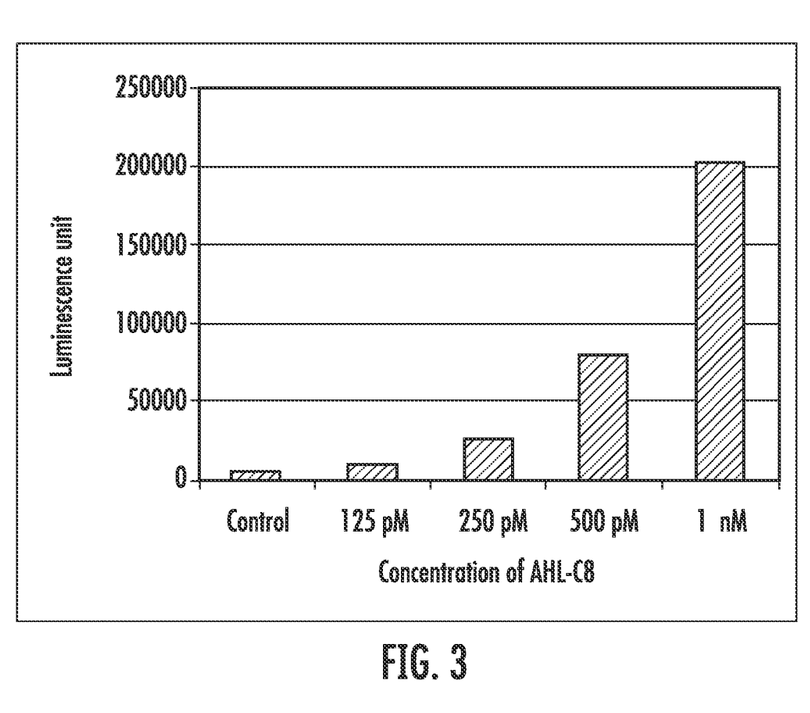
FIG. 3 shows a luminescence assay using the cell-lysate extract and Beta-Glo system for detection of acyl-homoserine lactone (AHL-C8).
Figure 4:
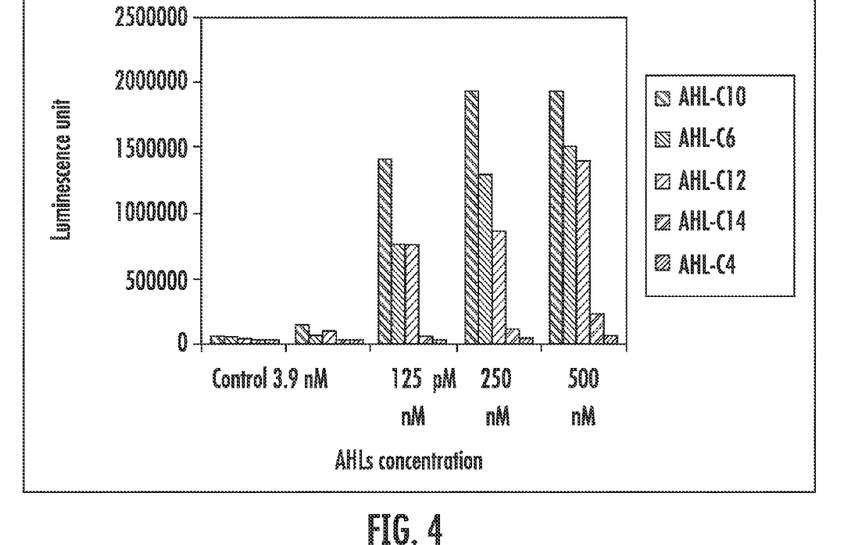
FIG. 4 shows a luminescence assay using the cell-lysate extract and Beta-Glo system for detection of various acyl-homoserine lactones (AHL-C4, AHL-C6, AHL-C10, AHL-C12, and AHL-C14).
Figure 5A:
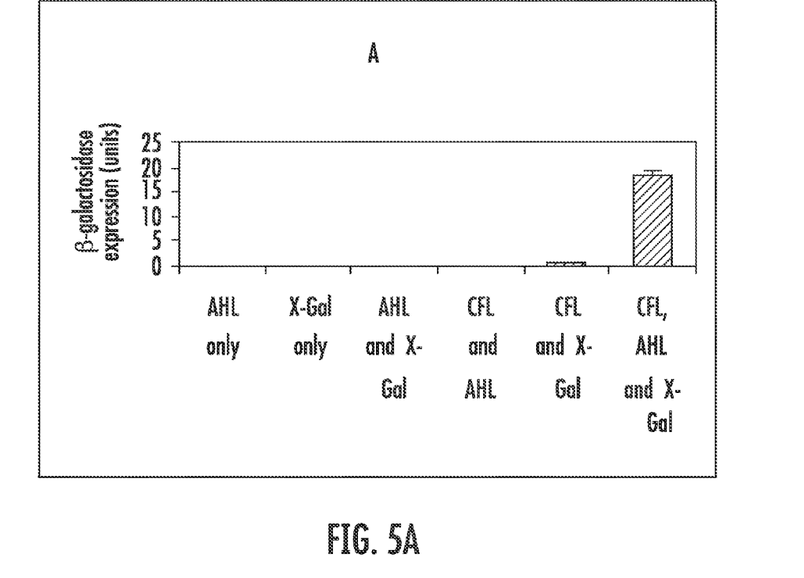
FIG. 5 shows charts that confirm β-galactosidase expression in the in vitro cell-free solution: (A) Components required for Reactions 1) through 3). These reactions include: 1) binding of AHLs with the reporter protein TraR; 2) binding of TraR/AHL complex to the traR promoter driving the expression of the β-galactosidase. (B) Inhibition of Reaction 1) with high temperature. (C) Inhibition of Reactions 2) and 3) by streptomycin. Bars indicates means±standard deviation (n=3).

Results of negative- and positive-controls, consisting of cell-free assays conducted with- and without X-Gal and $C_8$-AHL (FIG. 5A), respectively, showed that, as expected, unless both $C_8$-AHL and X-Gal were added into cell-free assay solution, β-galactosidase activity remained minimal. Controls, having addition of X-Gal but no AHL, exhibited minimal background β-galactosidase activity in the cell-free extract.

Figure 5B:
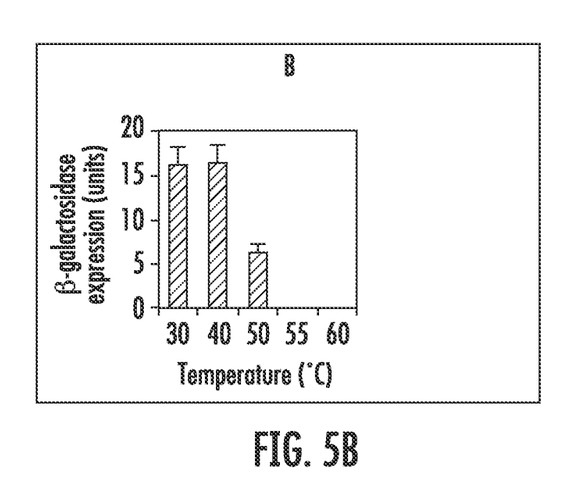
Figure 5C:
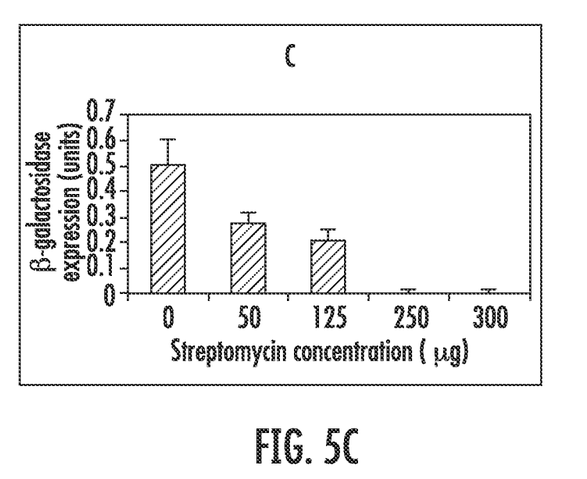
Figure 6:
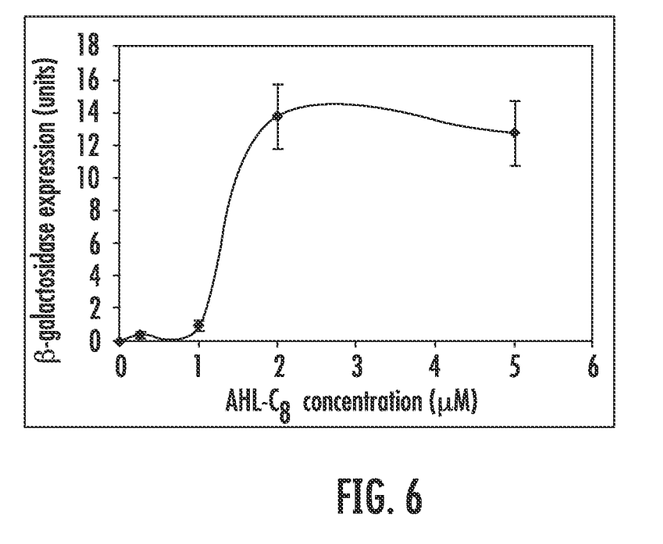
FIG. 6 shows a dose-response curve of β-galactosidase expression in a cell-free lysate with addition of C8-AHL. Points represent mean values of three samples. Error bars represent standard deviations.

Results of β-galactosidase activities showed that detection of AHLs, using the cell-free assay using the cell-free extract, was deactivated above 55° C. (FIG. 5B). Therefore, β-galactosidase expression did not occur when pre-treatment of cell-free extracts with high temperature (e.g. 55° C. and 60° C.) were followed by addition (at 30° C.) of $C_8$-AHL. Further, streptomycin additions above 125 µg/ml reduced assay activities (FIG. 5C). Results of $C_8$-AHL additions, showed that absorbance changes (i.e. blue color at 635 nm), resulting from the enzymatic cleavage of the chromogenic substrate X-Gal, were proportional to concentration, up to 2 µM $C_8$-AHLs (FIG. 6).

Optimization of Cell-Free Assay.

Crude Protein Concentration in Cell-Free Extract Solution.

Figure 7A:
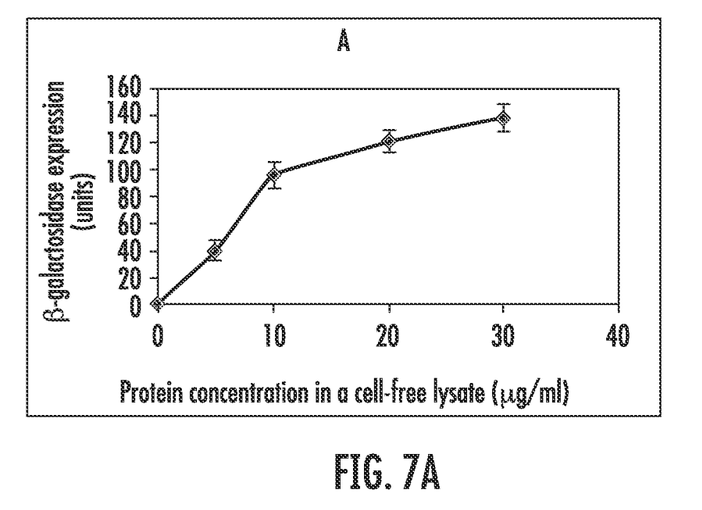
FIG. 7 shows optimization of cell-free assay conditions. (A) Crude protein concentrations in a cell-free extract solution. (B) Optimum pH for a cell-free assay. (C) Incubation times for cell-free assays. Values (points or bars) indicate means±SD (n=3).

Crude protein concentrations, ranging from 6 µg/ml to 30 µg/ml resulted in a non-linear increase of β-galactosidase expression with time (FIG. 7A).

Determination of Optimum pH.

Figure 7B:
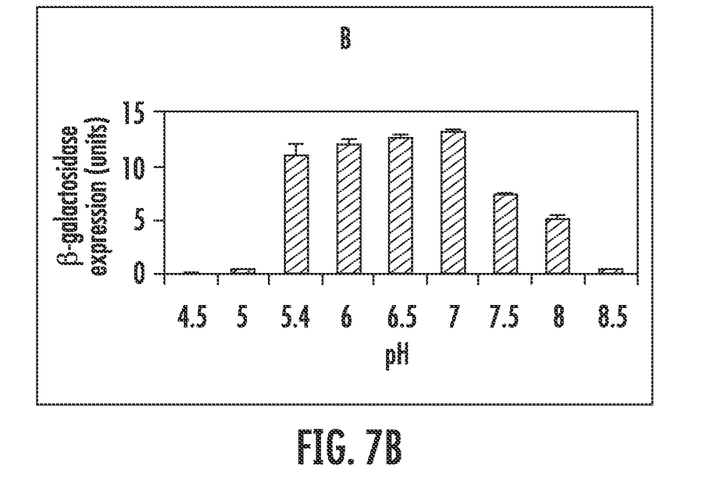

Results of incubations examining the effect of pH on β-galactosidase expression in the cell-free assay (FIG. 7B) showed that the highest β-galactosidase expression occurred between pH 6-7, while expression declined dramatically at pH 7.5 or higher. Therefore, pH 6.5 was chosen for the measurement conditions for the cell-free assay. Since the assay was very sensitive to pH, reducing the volume of sample to maintain the pH of whole assay solution was important.

Incubation Time.

Figure 7C:
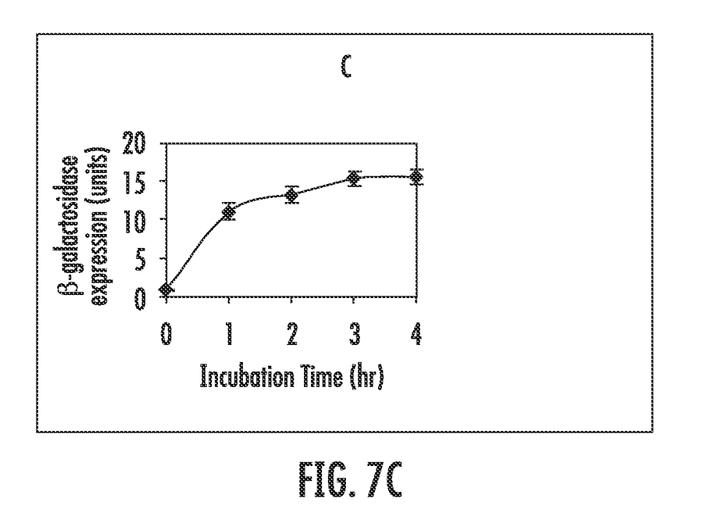

Incubation time affected β-galactosidase expression (FIG. 7C). Increasing assay incubation times from one to four hours resulted in an asymptotic increase in expression of β-galactosidase activity for a given concentration of added AHL. In order to make the cell-free assay system rapid and practical, a 2 h incubation was chosen for our assays.

Comparison of Absorbance and Luminescence Assays.

The cell-free assay was not able to detect $C_4$- and $C_{14}$-AHLs. Using the luminescence substrate Beta-Glo®, detection of various AHLs was approximately 10-fold more sensitive, when compared to absorbance assays. Table 1 shows minimum concentrations of each AHL resulting in an induction ratio greater than 3 in cell-free absorbance and luminescence assays. Values represent means±SD (n=3).

TABLE 1

| AHL | Luminescence assay | Absorbance assay |
| --- | --- | --- |
| $C_4$-AHL | — | — |
| $C_6$-AHL | 30 ± 3 nM | 335 ± 10 nM |
| $C_7$-AHL | 25 ± 5 nM | 245 ± 8 nM |
| $C_8$-AHL | 20 ± 2 nM | 225 ± 11 nM |
| $C_{10}$-AHL | 100 ± 5 nM | 1300 ± 20 nM |
| $C_{12}$-AHL | 200 ± 6 nM | 2400 ± 30 nM |
| $C_{14}$-AHL | — | — |
| oxo-$C_6$-AHL | 17 ± 2 nM | 180 ± 25 nM |
| oxo-$C_8$-AHL | 10 ± 3 nM | 120 ± 10 nM |

Application of Cell-Free Assay for Screening Genomic Clones for the Identification of Putative luxI Homologs.

To demonstrate one possible application of the newly-developed cell-free assay, a genomic library was constructed from the SRB isolate, *Desulfovibrio* H2.3jLac, and screened for putative QS activity using the cell-free assay. Results of screening (~5× genome coverage) revealed that 24/500 fosmid clones demonstrated positive reactions ranging from a high- to a low-level of activity. Then, production of several AHLs ($C_6$-AHL, oxo-$C_6$-AHL, $C_8$-AHL, $C_{10}$-AHL and $C_{12}$-AHL) by positive clones was confirmed by mass spectrometry (results not shown). Further studies are currently underway to identify the genes involved in the production of AHLs by *Desulfovibrio* H2.3jLac.

Summary

The luminescence assay has increased sensitivity over the absorbance-based assay. It can detect AHL-C7, -C8, and -oxo-C6 at minimum detection limit of approximately 10 nM. For AHL-C6, -C10, and -C12, low µM level can be detected.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of detecting a quorum sensing signal in a bacteria sample, the method comprising:
   adding a detecting substrate and the cell-lysate extract solution to a well of a microtiter plate to form an assay reagent configured to report the detection of the quorum sensing signal, wherein the detecting substrate is an absorbance-based substrate or a luminescence-based substrate, and wherein the cell-lysate extract solution is formed from *Agrobacterium tumefaciens* NTL4 (pCF218)(pCF372);
   adding the bacteria sample to the well;
   incubating the bacteria sample within the well in the presence of the cell-lysate extract solution;
   measuring absorbance or luminescence of the assay reagent in the presence of the bacteria sample within the well; and
   determining the presence or absence of quorum sensing signals in the bacteria sample, wherein the quorum sensing signal comprises an acyl-homoserine lactone.

2. The method as in claim 1, wherein the assay reagent is an aqueous-based solution comprising the detectable substrate and the cell-lysate extract solution.

3. The method as in claim 1, wherein the detecting substrate comprises an absorbance-based substrate.

4. The method as in claim 3, wherein the absorbance-based substrate comprises 5-bromo-4-chloro-3-indolyl-β-D-galactopyransoside.

5. The method as in claim 3, wherein absorbance is measured by:
   applying a light having a specific wavelength to the assay reagent in the presence of the bacteria sample, and
   measuring any absorbance of the sample at the specific wavelength.

6. The method as in claim 1, wherein the detecting substrate comprises a luminescence-based substrate.

7. The method as in claim 6, wherein the luminescence-based substrate comprises 6-O-β-galactopyranosyl luciferin.

8. The method as in claim 6, wherein luminescence is measured by reading the luminescence of the sample using a luminometer.

9. The method as in claim 1, wherein forming the cell-lysate extract solution from the biosensor bacterium comprises:
   centrifuging a cell culture to create cell pellets;
   collecting the cell pellets comprising cells, wherein each cell comprises cellular contents surrounded by a cell membrane; and
   disrupting the cell membranes of the cells to release the cellular contents into an aqueous solution.

10. The method as in claim 9, wherein disrupting the cell membranes of the cells to release the cellular contents into the solution comprises:
    applying sound energy to the cells to disrupt the cell membranes and release the cellular contents.

11. The method as in claim 9, further comprising:
    centrifuging the aqueous solution to form the cell-lysate extract solution as a supernatant solution containing the cell contents separated from the cell wall membranes.

12. The method as in claim 1, wherein the bacteria sample is incubated with the well prior to adding the detecting substrate and the cell-lysate extract solution.

13. The method as in claim 12, further comprising:
    after adding the detecting substrate and the cell-lysate extract solution to the well, incubating the detecting substrate with the cell-lysate extract solution.

14. The method as in claim 1, wherein the detecting substrate and the cell-lysate extract solution are added after the bacteria sample is added to the well.

15. The method as in claim 2, wherein the assay reagent is a buffered aqueous-based solution comprising a buffering agent and having a pH that is balanced from about 5 to about 9.

16. The method as in claim 15, wherein the buffered aqueous-based solution has a pH that is balanced from about 6 to about 8.

17. The method as in claim 15, wherein the buffered aqueous-based solution comprises $KH_2PO_4$.

* * * * *